United States Patent [19]

Marshall

[11] Patent Number: 5,236,826

[45] Date of Patent: * Aug. 17, 1993

[54] IMMUNOASSAY FOR THE DETECTION OR QUANTITATION OF AN ANALYTE

[75] Inventor: David L. Marshall, Norcross, Ga.

[73] Assignee: Murex Corporation, Norcross, Ga.

[*] Notice: The portion of the term of this patent subsequent to Jan. 17, 2007 has been disclaimed.

[21] Appl. No.: 630,365

[22] Filed: Dec. 18, 1990

Related U.S. Application Data

[63] Continuation of Ser. No. 220,882, Jun. 22, 1988, abandoned, which is a continuation of Ser. No. 96,207, Sep. 8, 1987, abandoned, which is a continuation of Ser. No. 807,157, Dec. 10, 1985, abandoned.

[51] Int. Cl.$^5$ .......................................... G01N 33/543
[52] U.S. Cl. ................................. 435/7.92; 435/7.1; 435/7.9; 422/57; 436/518; 436/519; 436/524
[58] Field of Search ................. 435/7.1, 7.92; 422/55, 422/56, 58; 436/533, 534

[56] References Cited

U.S. PATENT DOCUMENTS

| | | | |
|---|---|---|---|
| 3,966,897 | 6/1976 | Renn et al. | 424/1.5 |
| 4,138,474 | 2/1979 | Updike | 436/535 |
| 4,184,849 | 1/1980 | Cambiaso et al. | 435/7 |
| 4,185,084 | 1/1980 | Mochida et al. | 436/518 |
| 4,191,739 | 3/1980 | Uzgiris et al. | 436/523 |
| 4,197,361 | 4/1980 | Hoff et al. | 436/531 |
| 4,200,436 | 4/1980 | Mochida et al. | 436/512 |
| 4,201,763 | 5/1980 | Monthony et al. | 436/533 |
| 4,233,286 | 11/1980 | Soothill et al. | 436/534 |
| 4,248,965 | 2/1981 | Mochida et al. | 436/531 |
| 4,338,094 | 7/1982 | Elahi | 23/230 |
| 4,388,296 | 6/1983 | Hart | 436/533 |
| 4,415,700 | 11/1983 | Batz et al. | 524/548 |
| 4,446,232 | 5/1984 | Liotta | 436/514 |
| 4,459,361 | 7/1984 | Gefter et al. | 436/523 |
| 4,486,530 | 12/1984 | David et al. | 435/7 |
| 4,508,831 | 4/1985 | Toth | 436/512 |
| 4,582,792 | 4/1986 | Kashahara et al. | 436/523 |
| 5,017,474 | 5/1991 | McClune et al. | 435/7.5 |

Primary Examiner—Christine Nucker
Assistant Examiner—Jeffrey Stucker
Attorney, Agent, or Firm—Jones, Askew & Lunsford

[57] ABSTRACT

An immunoassay method for the detection or quantitation of an analyte suspected of being in a solution comprising: (a) combining said specimen, a first binding component, insoluble particles, and second binding component labelled with a signal generating material in a solid phase retention and separation apparatus having a sufficient pore size such that said particles are trapped within said filter yet permitting rapid passage of fluid therethrough in such a manner that an immunological reaction occurs if analyte is present in said specimen, resulting in the formation of an immunocomplex of insolubilized first binding component:analyte:second labelled binding component on or within said filter means; (b) separating bound from unbound material; and (c) determining the presence and/or amount of signal produced which is correlative with the amount of analyte present in the solution.

3 Claims, No Drawings

IMMUNOASSAY FOR THE DETECTION OR QUANTITATION OF AN ANALYTE

This application is a continuation of application Ser. No. 220,882, filed Jun. 22, 1988, which is a continuation of application Ser. No. 07/096,207, filed Sep. 8, 1987, which is a continuation of application Ser. No. 06/807,157, filed Dec. 10, 1985, all abandoned.

BACKGROUND OF THE INVENTION

1. Field of the Invention

The field of this invention relates to a solid phase system for performing an immunoassay for detection and quantitation of an analyte suspected of being in a specimen. More particularly, the invention relates to a method using a solid support surface consisting of particles to which can be bound a binding component or antigen.

2. Prior Art

Numerous methods utilizing immunoassay techniques for more precise and reliable ways to quantitate an amount of analyte in a specimen. The rapid, quantitative and cost-efficient results desired by the medical and diagnostic testing industry have provided the impetus for novel means of accomplishing these goals. There are two types of assay systems currently used. One is a homogeneous system whereby the assay is performed in a single phase. Antibody and analyte are allowed to react together and a labelled material is introduced which binds to the antibody or antigen after an antibody:antigen complex has formed. The label generates a signal which is readable when present in the reaction zone or solution. The signal is correlative with the amount of analyte present in solution. This indirect measurement is generally used because of the difficulty of direct measurement of many analytes.

The second type of system is a heterogeneous assay which is a two-phase system where there is a solid, or bound, phase and a liquid, or an unbound phase, requiring an additional step so separate the bound from unbound material. Typically, a solid support surface is used as the bound phase, to which is attached an antibody or antigen via a chemical bond or adsorption. Various types of solid support surfaces have been developed to improve the efficiency of the immunological reaction between antibody and antigen, and, to increase the efficiency of the separation step. An inefficient or incomplete separation of bound from unbound can result in unbound label remaining in the reaction zone after the separation step, which will cause a positive signal to be read where there is no antigen present. An efficient binding and subsequent separation are two of the most important aspects of a desirable assay.

Particles have been used in agglutination assay procedures for some time in order to overcome the drawbacks of inefficient binding. In this type of system soluble antigens will combine with their specific antibody to form a precipitate, in which the antigen-antibody complexes form large aggregates which are insoluble. The same antigens, if attached to particulate matter such as latex particles or bacterial cells, will form agglutinates or clumps. The agglutination reaction can be detected and quantified using visual or instrumentation means such as light-scattering or absorption techniques (Bellanti, "Immunology II", W. B. Saunders Company, Philadelphia, 1978, p. 212). Though the test is commonly used in the clinical laboratory, it suffers from several limitations, such as serum interferences, sensitivity, and, most importantly, from the perspective of the techniican or scientist performing the test, the subjective judgment of the assay endpoint. While the method is convenient for qualitative analysis, it is inadequate for quantitative analytsis, especially of very low concentrations of analytes. Latex particles have been used as labels for the analyte of interest, whereby the assay relies on the use of an agglutination reaction to decrease the number of particles of a particular size present in the assay mixture (Boguslaski, et al., "Clinical Immunochemistry" Little, Brown and Company, Boston, 1984, p.211).

Various material have been used as support support surfaces, including glass rods, glass beads, silica impregnated strips, glass fiber, filter paper, cellulose or its derivatives, Sepharose beads, plane polymeric surfaces, magetizable solid phase cellulose/iron oxide particles, ferratin, etc.

Coated test tubes and trays have the limitation that only the inner surface of the vessel is coated with the solid phase. Material in the center of the solution will not be in intimate contact with the solid phase until and unless agitated; and even then only over a comparatively long period of time. The lack of surface area prevents the rapid establishment of an equilibrium between the bound and unbound phase.

Physical separation of the bound phase from the unbound phase is required in heterogeneous assays. Most often the bound phase is retained for measurement. Separation is generally accomplished by one of several methods including chromatography, filtration, electrophoresis, adsorption, precipitation, or centrifugation. It is preferable to use a method which is adaptable for use in automated equipment or in a system that can be used by a trained technician.

Thus, Michael E. Jolly, Ph.D., discloses in Pandex Laboratories Research Report No. 1, July 1983, a particle concentration fluorescence immunoassay wherein 0.6–0.8 um polystyrene particles are bound to the antigen of interest. A first antibody directed against the antigen and a labelled second antibody directed against the first antibody are contacted with the bound antigen. The label is limited to a fluorescent molecule and is read after separation by front-surface fluorimetry.

Such procedure contains deficiencies in that it is limited to fluorescent signal and detection means and it is also limited to front-surface reading; which does not appear to be pragmatic for rear surface viewing. Moreover, the particles disclosed are only composed of polystrene and 0.6–0.8 $\mu$m in size, rather than a broad range of useful particle compositions and sizes.

U.S. Pat. No. 4,201,763, issued to Monthony, et al., discloses water insoluble hydrophilic polymeric particles in the performance of a sandwich or competitive immunoassay. The method is limited to the use of a fluorescent label and therefore lacks the versatility of uses in situations where nonfluorescent labels are perferrable.

U.S. Pat. No. 4,415,700, issued to Batz, et al., describes hydrophilic latex particles consisting of a homo- or co-polymer of monomers containing at least one epoxy group and at least one polymerizable carbon-carbon double bond in the molecule. The method using the particles is a competitive assay wherein labelled first antibody bound analyte and unlabelled first antibody bound analyte compete for binding sites on a particle bound second (anti-first antibody) antibody. Again, the invention is limited to one type of label, in this instance an enzyme, and is also limited to a particular particle composition.

With the emergence of the physician's office and self-testing markets, there is a need for a separation technique that can be used by relatively unskilled users. A solid phase that would be compatible with an easy-to-use separation system, that provided accurate and repeatable results would be advantageous. Such a method should have a solid phase that permits a rapid equilibrium to be established between the antibody and antigen so as to promote rapid binding of the two; it should also be convenient and inexpensive; and, it should be usable in settings in addition to a hospital or laboratory, i.e., the physician's office or in the home.

SUMMARY OF THE INVENTION

The present invention relates to a method for performing a heterogeneous immunoassay for the detection and quantitation of an analyte suspected of being in a specimen which overcomes the problems heretofore encountered.

More particularly, the present invention is directed to a method comprising a relation between finely divided particulate solid material capable of forming a stable suspension in a liquid medium and an insert porous filter matrix means of sufficient pore size to retain the particles on or within the filter matrix, yet permitting the flow of liquid therethrough. Material thus retained remains available to interact in subsequent assay procedures.

A solid phase is provided to which has been bound a binding component. In the performance of the assay, which can be simultaneous or sequential, an analyte in solution is mixed with an amount of particle-bound binding component and allowed to react. A second binding component labelled with a signal-generating material, is added and likewise allowed to react, forming an immunocomplex of particle-bound binding component:antigen:labelled second binding component. The complex is then washed to remove unbound labelled binding component and the reaction area read to measure the amount of signal present, which is correlative with the presence or quantity of analyte present in the specimen.

DESCRIPTION OF THE INVENTION

This invention is directed to a binding component attached to a particulate material used as a solid phase in a heterogeneous immunassay procedure.

In the course of the invention described herein the following terms will be described and have the following applied meanings:

binding component—any molecule, compound, or combination thereof capable of recognizing and binding to a distinct spatial or polar organization of a molecule (commonly referred to as an antigenic determinant or an idiotype);

solid phase—material that has been rendered insoluble by binding to the particulate material, as distinguished from the liquid phase which contains soluble material;

label—a substance that generates or can be made to generate a signal capable of being detected or measured by visual or instrumentation means; and analyte (of interest)—a compound, substance or organism suspected of being present in a patient sample solution; the presence or absence of which is of interest to the user, and which contains at least one unique spatial or polar organization capable of being recognized and bound by a binding component.

Solid phase immunoassays generally use some type of solid support surface to which can be bound, directly or indirectly, components which are thereby rendered insoluble with respect to the liquid medium in which the components were dissolved. The principle involved is that by removing the material from the liquid phase, and subsequently washing the solid phase, a more complete separation can occur, which increases the overall sensitivity of the assay. To this end various types and structures of materals have been chosen for different purposes. Systems use sheets of filter paper, glass, cellulose, or like types of materials, to which the binding component is attached. In some cases the inner or outer surface of a test tube or microtiter tray well is used so as to provide simultaneously a reaction vessel integral with the solid phase. Additionally, beads of various compositions have been used in an effort to increase the surface area of the solid support surface material.

The present invention uses a novel relation between finely divided particulate solid material capable of forming a stable suspension in a liquid medium and an inert porous filter matrix means of sufficient pore size to retain the particles on or within the filter matrix, yet permitting the flow of liquid therethrough. Material thus retained remains available to interact in subsequent assay procedures such as but not limited to washing to deparate bound form unbound material, reagent addition, optical measurement, and the like.

The particles can be made of any solid material that meets two requirements. First, it must be suspendable in solution; by this is meant that the particles are insoluble in solution but are small enough to be suspended in the solution. This increases favorable reaction kinetics through Brownian motion, thereby establishing equilibrium faster than a system with less available surface for binding. Second, the material must be filterable: particulate material is capable of being retained on or within a semi-permeable substance, preferably inert with respect to the chemical reactions. Filter material is composed of a substance such as paper, glass fiber, scintered glass, cotton, synthetic polymer, plastic, cellulose, cellulose acetate, polytetrafluoroethylene, polyethylene, polypropylene or polyvinylidine fluoride, and the like. The particles can be made of a wide variety of materials including, but not limited to, glass, cellulose, synthetic polymers or plastics, proteins (e.g., gluteraldehyde or albumin), bacterial cells (e.g.), protein A staphylococcus), and the like. Latex is a preferred material because of its availability, cost-effectiveness and ease of use.

The size of the particles is limited, again, only by the requirements of suspendability and filterability. The particles should be large enough to be trapped by a given filter material, yet small enough to be suspendable in a liquid medium. They are preferably spheroidal in shape, but the structural and spatial configuration is not critical; for instance, the particles could be slivers, ellipsoids, cubes, and the like. A suitable particle size ranges from a diameter of 0.2 $\mu$m to 50.0 $\mu$m, preferably between 0.4 $\mu$m to 1.0 $\mu$m.

It is also possible to use as a solid particle organisms which can bind to the antibody directed against them. In such an embodiment the organism would be of a size or diameter that would be suspendable and filterable. An example is *Toxoplasma gondii*, a parasite of micron dimensions which binds to the antibody specific for it.

A labelled anti-antibody directed against the *Toxoplasma gondii* antibody is used to attach a signal generator to the complex.

While the specific particle size is relevant, the primary focus is on the relationship between the particle size, filter thickness and filter pore size. The filter pore size is defined by the construction of the filter material. In the case of glass fiber filters the size density of the fibers defines the amount and size of the interstices therein. The filter is designed to contain pores or interstices large enough to entrap particles within or on the filter and prevent their passing therethrough. Moreover, the width or thickness of the filter should be sufficient to permit an effective amount of particles to become entrapped. Were the filter too thin, there sould be inadequate space for enough particles to be entrapped to perform a quantitative assay.

It is preferable for the particles to be caught within the filter, but some of the particles will remain blocked on its surface, whether because of clumping, aggregation or random nonuniformly sized particles. One advantage of interstice or pore entrapment is the favorable reaction kinetics that result. When the particles are immobilized within the porous filter and fluid must be contacted with the surface of the particles, such as in a wash step, there is greater surface area availaable for contact if the particles are suspended, as it were, in the filter, with their surfaces virtually completely exposed to the fluid in contact therewith. Where the particles are trapped solely on the surface of a thin membrane incapable of retaining particles in a three dimensional network of pores or interstices, there is less surface area available because the particles are in contact with each other, resulting in a decreased surface area; therefore, a less efficient wash or fluid contact occurs, decreasing the efficience of the assay procedure.

Another advantage of internal, as opposed to external, entrapment is the convenience of physical transport of devices embodying the assay materials. Where particle bound binding component is pre-spotted in the filter, lyophilized, or otherwise immobilized, the filter effectively binds the particles with little possibility of the particles dissociating from the filter during rough handling. Where particles are pre-spotted on top of the surface of a thin membrane, there is a greater likelihood of the particle layer coming off the membrane if dropped, jostled or otherwise disturbed. Additionally, if the particles are deposited as a layer on a membrane, and dried thereon, when reconstituted the layer might float off the membrane and shift its position, potentially reducing the amount of material within a narrowly defined reaction zone. This deficiency is not present in the instant invention because pre-spotted particles are securely immobilized within the filter and not subject to the same mistreatment. It is inevitable, however, that a certain fraction of the particles will be blocked on the surface of the filter. The method of theis invention comtemplates the enablement of the procedure regardless of the amount of surface entrapment that occurs.

The filter itself has the unique characteristic of being able to wick fluid away from the point of application by capillary action while the particles are entrapped in the filter matrix. This permits a large volume of fluid to be transported from an area in contact with the particles and other bound components and to an area away therefrom. Since the efficiency of an assay technique is, in part, dependent upon the completeness of separation between bound and unbound material, the greater the volume of wash fluid that is in contact with the components, the more effective the wash. The completeness of the wash reduces the amount of background noise present where unbound signal generating material remains in the zone of measurement. The filter contemplated by the present invention can provide an improved means for accomplishing this desired separation.

The particles have bound to them a binding component, which is rendered insoluble. The binding component is chosen to be able to recognize and bind to an analyte in solution. Typically, where the analyte is an antigen (any substance capable of eliciting an immune response, e.g., group A strep or human chorionic gonadotropin) the binding component is an antibody that will bind to an antigenic determinant on the antigen. Where the analyte is an antibody, such as when testing for rubella or hepatitis, the binding component is an antigen. It is also possible for the analyte to be an antibody and the binding component to be an (anti)antibody directed to the analyte antibody. Moreover, it is useful to employ monoclonal antibodies for the particle-bound binding component as well as for the labelled binding component because of the high degree of selectivity and sensitivity associated with such antibodies.

The binding component can be directly attached to the Particle material via absorption or covalent chemical bonding, the methods for which are well known in the art. Direct adhering of binding component can be achieved by reacting carbodiimide with the particle and the binding component. Alternatively, serum Protein A is used in a well known procedure. Indirect insolublization of binding component can be achieved by attaching to the particle material a member of a binding pair, such as biotin, and separately attaching to the binding component the other member of the binding pair, such as avidin. When particle-bound biotin is mixed with the binding component-bound avidin the avidin and biotin bond together, forming a particle-avidin-biotin-binding component linkage. Such a method would be advantageous when it is desirable to insolublize the binding component:analyte complex after it has formed, rather than before. Another technique for indirectly attaching the binding component to the particle material is by binding an antibody to the particle material, separately binding to the binding component a different, (anti)antibody directed against the particle-bound antibody and subsequently mixing the products of each reaction together to form a particle-antibody:(anti)antibody-binding component structure.

Where latex particles and glass fiber filter paper is used, conditioning of the filter is necessary prior to, or contemporaneously with, the addition of insolublized material to the filter means. The purpose is twofold; first, to enhance the immobilization of latex particles within the interstices; second, to prevent the nonspecific sticking of unbound antibody or other extraneous materials to the filter. The conditioning material can be different for both, such as but not limited to gelatin, horse serum, albumin, dry milk, and the like. The material can be added to the filter prior to the addition of commponents to the filter. Alternatively, the conditioning material may be added simultaneously with the other reactants, or, it can even be mixed with the specimen fluid as a diluent or the particle suspension.

The particles coated with binding component are then contacted in a reaction vessel or container with a biological fluid suspected of containing an analyte such as bacterial, viral, fungal or parasitic antigens and immunoglobulins, antibodies, hormones, serum proteins, enzymes, drugs, and the like. Biological fluids from which samples can be obtained include urine, feces, blood, serum, mucus, sputum, semen, and the like. Analyte will form an immunological complex with the insolublized binding component.

Simultaneously, or subsequently, depending on the assay procedure, a second binding component labelled with a signal-generating material is added to the reaction vessel. This labelled binding component commonly is an antibody, directed against the analyte. The antibody has been conjugated with a label prior to its addition to the reaction vessel. Several types of labels are available for use in the present invention, depending upon the type of assay being conducted, including enzyme, luminescent, bioluminescent, chemi-luminescent and radioisotopic materials. The label must be capable of emitting or assist in emitting a signal detectable by visual or instrumentation means. The labelled binding component will bind to the complex thereby providing an indirect means for identifying the presence and quantity of analyte present in the reaction vessel.

The newly formed insoluble immunocomplex of insolublized binding component:analyte:labelled binding component is then washed to remove unbound material which could interfere with the accurate representation of the label present; namely, label which has nonspecifically bound to material in the reaction vessel other than the insolubilized immunocomplex, such as proteins, the reaction vessel itself or the particles. The separation is conducted by a filtration procedure involving passing through or into a filter material the reaction mixture, which is retained because of its size in the filter interstices. The immunochemical reactions can occur within the filter or external thereto. Unbound materials wash through or out of the filter and away from the reaction zone which is to be read. Separation is accomplished by passing fluid through the filter by gravity, capillary action, or by using positive or negative pressure, such as a vacuum or pump. The completeness of the separation is critical to the sensitivity of the assay; the more unbound material which could emit a detectable signal that is removed the less background noise there will be to interfere or obscure a weak signal being emitted from a very low concentration of bound label.

The wash solution can be a buffer, such as phosphate or TRIS, or any other solution appropriate and compatible with the components involved. Where an enzyme label is used the substrate may be added as part of the wash solution or separately added prior to reading.

The signal is read after any necessary developing, quenching or other modification of the signal. Reading can be done visually or through an instrument, such as a colorimeter to measure color absorbance where an enzyme label is used; a photometer to measure visible light where a luminescent, bioluminescent or chemiluminescent label is used; or a scintillation or gamma counter to measure radiation where a radioisotope is the label. The amount of signal produced is correlative with the concentration of analyte present in the biological sample fluid; the measurement is useful in diagnosis or monitoring drug levels or disease states.

The preferred embodiment of this invention is a sandwich enzyme immunoassay where the binding component is an antibody and attached to latex particles; the analyte is an antigen; the label is an enzyme; and the substances are added sequentially to a filter material, in which the separation occures. After washing the insolublized complex a substrate is added to produce a visual indication if antigen is present. The reaction area can also be read by an instrument to provide a sensitive quantitation of the antigen. An advantage of sequential addition is the greater degree of control over the binding reactions that is obtained. For example, where a very low concentration of antigen is suspected of being present, a longer incubation period is required because of the slower reaction kinetics involved; equilibrium will take longer to achieve. The result of the flexibility and control gained is the increased sensitivity for a quantitative measurement of analyte.

Another embodiment of this invention is the simultaneous addition of insolublized binding component, analyte and labelled binding component. An advantage of this embodiment is the elimination of the separate addition steps, thereby saving time for the user. This method is particularly useful where only a qualitative "yes-no" result is desired.

A further embodiment of this invention is a competitive assay whereby sample analyte and labelled analyte compete for binding sites on the insolublized binding component.

Still another embodiment of this invention is the pre-spotting of particle-bound binding component in the filter material or separation medium prior to the addition of analyte and other substances. This embodiment has the advantage of allowing for storage of a test device whereby the filter material has been pretreated with a particular particle-bound binding component enabling a user to perform an assay for a desired analyte and elimate one step of manipulation, thereby reducing the time and error associated an assay. Furthermore, this embodiment eliminates the step of separately adding the particle bound antibody, thus simplifying the procedure.

An alternative embodiment of this invention utilizes a plurality of monoclonal antibodies insolublized on or within the filter matrix and are designed to recognize and bind different and distinct analytes simultaneously. A plurality of labels of different wavelengths are used to identify the particular analyte and a photometer or other appropriate instrument, used to measure the intensity of the of the signal at the different corresponding wavelengths. In this manner it is possible, in a single test device or reaction area, using a single procedure, to obtain accurate and sensitive determinations of multiple antigens in a patient sample. A significant example of this is an assay for Gonorrhea and Chlamydia, a test frequently needed in hospitals and physicians' offices. Such a test, using monoclonal antibodies to the Gonorrhea and Chlamydia viruses bound to insolublized particles and a single reaction zone or container, could determined whether either, both or neither of the two diseases was present, employing only a single procedure.

Moreover, using the high selectivity of monoclonal antibodies, this invention could be used to detect the serotype of a particular bacteria, virus, paratsite, or other organism where e treatment would be different depending on the particular pathogen present.

Where enzyme labelling is desired a plurality of substrates is use each producing a signal readable by a photometer with monochromatic light. By scanning the spectrum, or using specific wavelengths, the instrument could distinguish the different wavelength signals, which the human eye would normally interpret as one average color.

The Examples which follow futher define and illustrate various embodiments of Applicant's invention. They are by way of illustration only and not by way of limitation. Other methods are contemplated as being within the scope and spirit of this invention.

Examples

Example 1

Procedure for Sequential Assay

A test to determine the presence of human chorionic gonadotropin (hCG) as an indication of pregnancy is performed on a urine specimen.

First, 5 drops of 0.5% gelatin in Tris buffered saline are added to a glass fiber filter paper (Micro Filtration Systems) to condition the filter. Then 4 ml of 2.5% latex particles (average diameter of 1 um, Polysciences) are added to 1 mg/ml solution of monoclonal antibody directed against hCG and mixed for three hours, then centrifuged. One drop of the urine specimen is added to 1 drop of the antibody-coated latex particles and the mixture permitted to incubate for one minute. One drop of a second monoclonal antibody directed against a different and distinct epitope on the hCG molecule and labelled with alkaline phosphatase is then added and the mixture is added to the filter and the filtrate washed with 1 ml Tris buffer solution. One drop of indoxyl phosphate substrate is added to the washed mixture to develop color. Appearance of a blue color is indicative of a positive result.

Example 2

Procedure for Simultaneous Sandwich Assay

The procedure according to EXAMPLE 1 is used; but, the antibody coated latex particles, urine specimen and labelled second antibody are mixed simultaneously and then incubated. Again, appearance of a blue color indicates a positive result.

Example 3

Procedure for Simultaneous Competitive Assay

A test to determine the presence and/or quantitation of digoxin.

First, 5 drops of 0.5% gelatin in Tris buffered saline solution are added to a glass fiber filter paper (Micro Filtration Systems) to condition the filter. Then 4 ml of 2.5% latex particles (1 um average diameter, Polysciences) are added to 1 mg/ml solution of a monoclonal antibody directed against digoxin and mixed for 3 hours, then centrifuged. One to 10 drops of a serum specimen suspected of containing digoxin and 1 drop of alkaline phosphatase labelled digoxin are combined with an excess amount of latex coated monoclonal antibody and incubated for 1 hour. The mixture is added to the filter and washed with 1 ml of Tris buffered saline to remove unbound digoxin. Then 1 drop of indoxyl phosphate substrate is added to the washed mixture. The appearance of a blue color is indicative of the presence of digoxin.

Example 4

Procedure for Sequential Competitive Assay

A test to determine the presence of thyroid stimulating hormone (TSH).

First, 5 drops of 0.5% gelatin in Tris buffered saline are added to a glass fiber filter paper (Micro Filtration Systems) to condition the filter. Then, 4 ml of 2.5% latex particles (average diameter of 1 um, Polysciences) are added to 1 mg/ml solution of a monoclonal antibody directed against TSH and mixed for 3 hours, then centrifuged.

One to 10 drops of alkaline phosphatase conjugated TSH are added to 1 drop of the latex bound monoclonal antibody and incubated. The mixture is added to the conditioned filter and washed with 1 ml of Tris buffered saline to remove unbound material. One drop of blood serum specimen suspected of containing TSH is added to the filter and allowed to react. The mixture is again washed with Tris buffered saline to remove unbound material. Then, 1 drop of indoxyl phosphate is added. The appearance of a blue color is indicative of the presence of TSH. A quantitative measurement of TSH can be made by reading the reaction zone with a colorimeter or similar instrument.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. An immunoassay for the detection or quantitation of an analyte suspected of being present in a specimen solution comprising:
    (a) contacting said specimen solution with insoluble particles capable of being suspended in said specimen solution and of binding any said analyte present in said specimen solution,
    (b) applying said suspension to a filter means having a pore size, such that said insoluble particles and insoluble complexes of said insoluble particles and said analyte, if any, are trapped within or on said filter means, and unbound material passes therethough
    (c) applying a soluble labeling component capable of binding to said analyte, to said insoluble particles and insoluble complexes, if any, on said filter means to form insoluble complexes of said insoluble particles, said analyte, and said labeling component, if any complexes of insoluble particles and analyte are present within or on said filter means, and
    (d) determining the presence or amount of signal produced by any said complexes of said insoluble particles, said analyte, and said labeling component as an indicator of the presence and/or amounts of said analyte present in the specimen solution.

2. An immunoassay method for the detection or quantitation of an analyte suspected of being present in a specimen solution comprising:
    (a) contacting said specimen solution with insoluble particles capable of binding said analyte and a soluble labeling component capable of binding said analyte to form a suspension of insoluble complexes of said insoluble particles, said analyte, and said labeling component, if any said analyte is present in said solution,
    (b) applying said solution to a filter means having a pore size such that said insoluble particles and insoluble complexes, if any, are trapped within or on said filter means and unbound material passes therethrough, and
    (c) determining the presence amount of signal produced by any said complexes as an indication of the presence or amount of analyte present in said specimen.

3. An immunoassay method for the detection or quantitation of an analyte suspected of being present in a speciment solution comprising:
   (a) applying insoluble particles capable of binding said analyte to a filter means having a pore size such that said insoluble particles are trapped within or on said filter means and unbound material passes therthrough,
   (b) contacting said trapped insoluble particles sequentially with said specimen solution and then with a soluble labeling component capable of binding said analyte to form insoluble complexes of said insoluble particles, said analyte, and said labeling component if any said analyte is present in said solution, and
   (c) determining the presence or amount of signal produced by any said complexes as an indicator of the presence or amount of analyte present in said specimen solution.

* * * * *